(12) United States Patent
Farvardin et al.

(10) Patent No.: US 12,343,033 B2
(45) Date of Patent: Jul. 1, 2025

(54) METHOD AND SYSTEM FOR ESTIMATING TEMPERATURE OF AN ULTRASONIC INSTRUMENT

(71) Applicant: Verb Surgical Inc., Santa Clara, CA (US)

(72) Inventors: Amirhossein Farvardin, San Jose, CA (US); Berk Gonenc, San Jose, CA (US); Steven Boronyak, Cincinnati, OH (US); Sean Conlon, Loveland, OH (US); Bernhard Fuerst, Mountain View, CA (US)

(73) Assignee: Verb Surgical Inc., Santa Clara, CA (US)

(*) Notice: Subject to any disclaimer, the term of this patent is extended or adjusted under 35 U.S.C. 154(b) by 510 days.

(21) Appl. No.: 17/723,411

(22) Filed: Apr. 18, 2022

(65) Prior Publication Data
US 2023/0329741 A1    Oct. 19, 2023

(51) Int. Cl.
*A61B 17/32*    (2006.01)
*A61B 17/00*    (2006.01)

(52) U.S. Cl.
CPC ............ *A61B 17/320068* (2013.01); *A61B 17/320016* (2013.01); *A61B 17/320092* (2013.01); *A61B 2017/00084* (2013.01); *A61B 2017/00199* (2013.01); *A61B 2017/320075* (2017.08)

(58) Field of Classification Search
CPC .... A61B 17/320068; A61B 17/320016; A61B 17/320092; A61B 2017/00084; A61B 2017/00199; A61B 2017/320075; A61B 2017/00119; A61B 2090/064; A61B 2090/065; A61B 2017/0003
See application file for complete search history.

(56) References Cited

U.S. PATENT DOCUMENTS

| | | | |
|---|---|---|---|
| 10,955,387 B2 | 3/2021 | Ross et al. | |
| 2003/0105480 A1 | 6/2003 | Wiener et al. | |
| 2009/0209900 A1* | 8/2009 | Carmeli | A61B 17/22012 600/12 |
| 2011/0017801 A1* | 1/2011 | Zemlok | A61B 17/07207 227/175.1 |
| 2012/0071796 A1* | 3/2012 | Smith | A61B 17/320092 601/3 |
| 2013/0331874 A1* | 12/2013 | Ross | G01N 29/44 702/19 |
| 2015/0073458 A1* | 3/2015 | Stoddard | A61B 17/320068 606/169 |

(Continued)

FOREIGN PATENT DOCUMENTS

KR    1020190062765 A    6/2019

OTHER PUBLICATIONS

PCT/IB2023/052083, "International Search Report and the Written Opinion of the International Searching Authority," Mailed Jun. 15, 2023, 9 pages.

*Primary Examiner* — Richard G Louis
(74) *Attorney, Agent, or Firm* — Aikin & Gallant, LLP

(57) ABSTRACT

A method performed by a surgical system. The method determines that an ultrasonic instrument is in a low-power state The method determines a resonance frequency of an end effector of the ultrasonic instrument and determines a temperature of the end effector based on the resonance frequency. A notification is displayed on a display of the surgical system based on the temperature.

23 Claims, 7 Drawing Sheets

(56) References Cited

U.S. PATENT DOCUMENTS

| | | | |
|---|---|---|---|
| 2019/0150898 A1 | 5/2019 | Kawasaki et al. | |
| 2019/0201040 A1* | 7/2019 | Messerly | A61B 17/07207 |
| 2019/0274720 A1 | 9/2019 | Gee et al. | |
| 2020/0132638 A1 | 4/2020 | Ross et al. | |
| 2021/0393310 A1* | 12/2021 | Nakamura | A61B 18/10 |

\* cited by examiner

METHOD AND SYSTEM FOR ESTIMATING TEMPERATURE OF AN ULTRASONIC INSTRUMENT

FIELD

Various aspects of the disclosure relate generally to surgical systems, and more specifically to a surgical system for estimating temperature of an ultrasonic instrument. Other aspects are also described.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a blade, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can be performed faster and with less surgeon fatigue using a surgical robotic system in which the surgical tools are operatively attached to the distal ends of robotic arms, and a control system actuates the arm and its attached tool. The tip of the tool will mimic the position and orientation movements of a handheld user input device (UID) as the latter is being manipulated by the surgeon. The surgical robotic system may have multiple surgical arms, one or more of which has an attached endoscope and others have attached surgical instruments for performing certain surgical actions.

Control inputs from a user (e.g., surgeon or other operator) are captured via one or more user input devices and then translated into control of the robotic system. For example, in response to user commands, a tool drive having one or more motors may actuate one or more degrees of freedom of a surgical tool when the surgical tool is positioned at the surgical site in the patient.

SUMMARY

A surgical tool that is used in some MIS procedures is an ultrasonic instrument that uses ultrasonic vibration at its tip to rapidly generate heat for cutting and cauterizing tissue. The tip may include a blade that reaches high temperatures (e.g., greater than 300° C.) during a "heating" cycle in which the blade oscillates against a piece of tissue, thereby producing heat due to friction between the blade and the tissue during the oscillation. After reaching a high temperature, the blade may be used to dissect a portion of tissue, while also sealing the remaining tissue. By performing multiple tasks (e.g., cutting for dissection, cauterizing, etc.), the use of the tool during a laparoscopic surgery reduces instrument exchanges and the number of instruments during the procedure.

Conventional laparoscopic surgical systems may be able to estimate a temperature of an ultrasonic instrument's blade during the blade's heating cycle. Specifically, such a system may activate the instrument by providing power (e.g., in response to receiving user input by an operator, such as pressing on a petal) for the instrument's blade to oscillate, as it is used to dissect tissue. While the instrument is active, the system may determine the temperature of the blade based on one or more characteristics (e.g., an input voltage, an input current, etc.) of the instrument. After the heating cycle is terminated (e.g., the operator releasing the petal), however, conventional systems cease powering the ultrasonic instrument. At this time, the blade enters a "cooling" cycle, where heat generated during the heating cycle is dissipated since the blade is no longer oscillating and therefore is not producing frictional heat. During this cooling cycle, conventional laparoscopic surgical systems do not provide the operator of the instrument with a real-time temperature of the blade. Specifically, these systems may be unable to determine the (e.g., current) temperature of the blade since characteristics that were used to determine the temperature during the heating cycle (e.g., input voltage) are no longer available because the instrument is not powered. As a result, if the operator were to manipulate surrounding tissues with the instrument while the blade was still hot (e.g., before the end of the cooling cycle at which the blade is below a temperature threshold), residual heat on the blade may inadvertently cause thermal injuries to potentially sensitive tissue. In addition, an operator may be unable to know with reasonable certainty the exact moment the residual heat has dissipated enough for the ultrasonic instrument to be used to manipulate (or touch) tissues without causing injury. For example, the temperature of the blade may vary during use based on the type/thickness of the tissue that the operator was actively cutting/cauterizing. As a result of the varying temperature, the blade may cool differently once a task is completed and the instrument enters its cooling cycle. Therefore, there is a need for surgical system that is configured to estimate (or predict) a temperature of an ultrasonic instrument, while the instrument is not using ultrasonic vibration to heat its blade (e.g., while in the cooling cycle).

The present disclosure provides a surgical system that estimates a temperature of an ultrasonic instrument, while the instrument is in a "low-power" state (or cooling cycle) in which the instrument does not draw (e.g., enough) power to heat an end effector of the instrument. The system determines that an ultrasonic instrument is in a "low-power" state (or cooling cycle) in which the ultrasonic instrument is not drawing (e.g., sufficient) power to heat the end effector, as the ultrasonic instrument would during a "high-power" state (or heating cycle) in which the ultrasonic instrument draws the power to heat the end effector. For instance, the ultrasonic instrument may be coupled to a generator that is arranged to provide current to the instrument based on received user input (e.g., the operator pressing on a pedal). With this current, the instrument may cause a blade of the end effector to vibrate to produce heat at high temperatures. While in this low-power state, however, the ultrasonic instrument may draw less power (e.g., to be provided less current) to cause the blade to vibrate less than while the instrument is in the high-power state. This lesser vibration may be insufficient for causing the blade to produce heat. While the ultrasonic instrument is in this low-power state, the system may determine a resonance frequency of the end effector (e.g., the blade while it vibrates over a lower excursion than needed to produce the heat). The system determines a temperature of the end effector based on the resonance frequency. For instance, the system may apply the resonance frequency (which may be at least one input) to a (e.g., predefined) model that produces the temperature as output. The system may display, on a display, a notification based on the temperature, such as displaying the determined temperature. Thus, the present disclosure is able to provide real-time temperature information to help the operator to assess whether the end effector is within a safe range for coming into contact with tissue, rather than having the operator speculate as to whether or not the end effector has cooled down.

In one aspect, the end effector may be a grasper that includes a blade (e.g., as one jaw) that vibrates along a longitudinal axis of the blade to produce the heat while the ultrasonic instrument is in the high-power state, as described herein. In addition, the grasper may include a hinged jaw that is rotatably coupled to a joint of the grasper, where the hinged jaw is arranged to rotate with respect to the blade to open or close the grasper. In some aspects, the resonance frequency may be determined in response to determining that the grasper is in an open position in which the hinged jaw is rotated away from the blade.

The above summary does not include an exhaustive list of all aspects of the disclosure. It is contemplated that the disclosure includes all systems and methods that can be practiced from all suitable combinations of the various aspects summarized above, as well as those disclosed in the Detailed Description below and particularly pointed out in the claims. Such combinations may have particular advantages not specifically recited in the above summary.

BRIEF DESCRIPTION OF THE DRAWINGS

The aspects are illustrated by way of example and not by way of limitation in the figures of the accompanying drawings in which like references indicate similar elements. It should be noted that references to "an" or "one" aspect of this disclosure are not necessarily to the same aspect, and they mean at least one. Also, in the interest of conciseness and reducing the total number of figures, a given figure may be used to illustrate the features of more than one aspect, and not all elements in the figure may be required for a given aspect.

DETAILED DESCRIPTION

Several aspects of the disclosure with reference to the appended drawings are now explained. Whenever the shapes, relative positions and other aspects of the parts described in a given aspect are not explicitly defined, the scope of the disclosure here is not limited only to the parts shown, which are meant merely for the purpose of illustration. Also, while numerous details are set forth, it is understood that some aspects may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
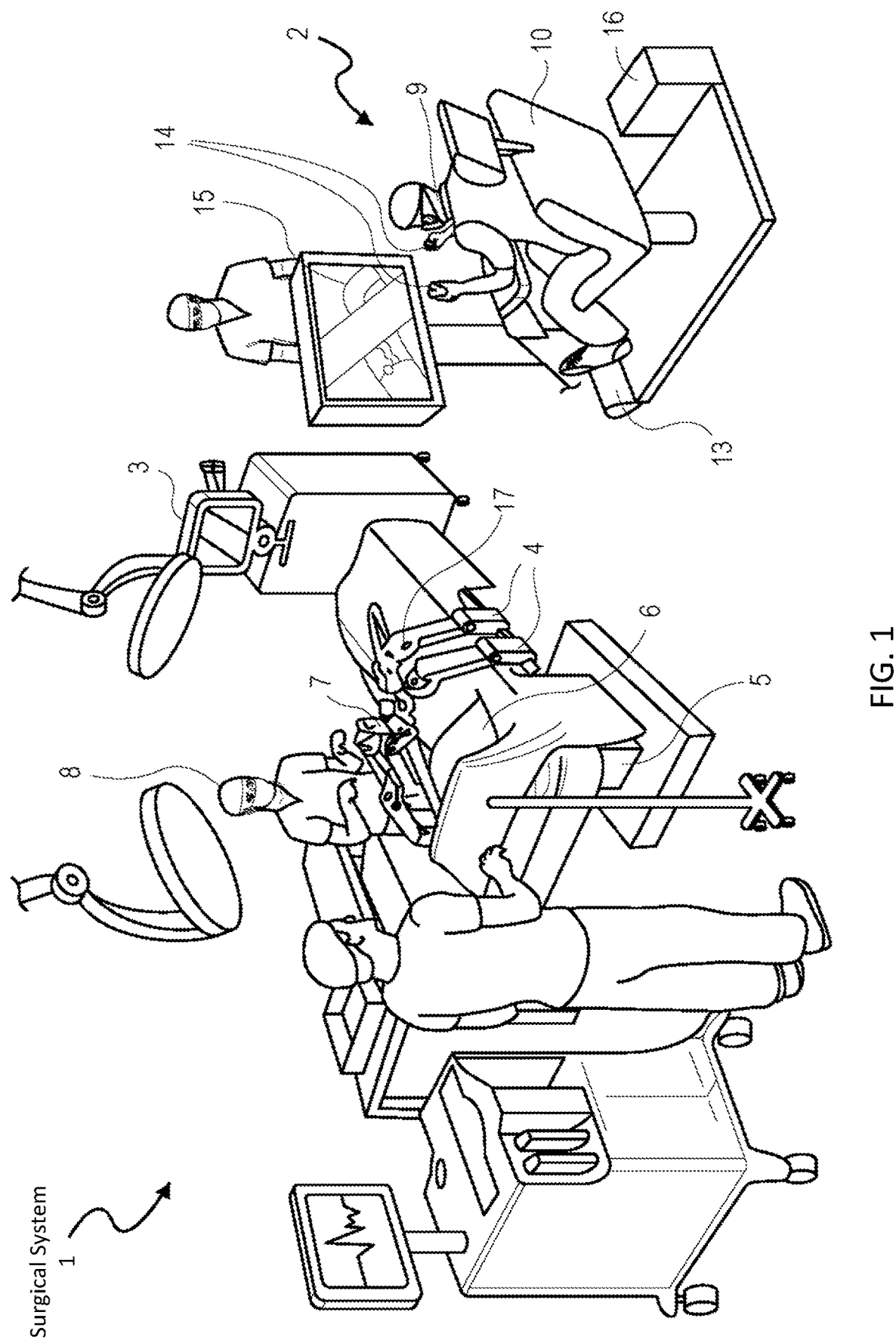
FIG. 1 shows a pictorial view of an example surgical system in an operating arena.

FIG. 1 shows a pictorial view of an example surgical system (which hereafter may be referred to as "system") 1 in an operating arena. The system 1 includes a user console 2, a control tower 3, and one or more surgical robotic arms 4 at a surgical robotic table (surgical table or surgical platform) 5. In one aspect, the arms 4 may be mounted to a table or bed on which the patient rests as shown in the example of FIG. 1. In one aspect, at least some of the arms 4 may be configured differently. For example, at least some of the arms may be mounted on a ceiling, sidewall, or in another suitable structural support, such as a cart separate from the table. The system 1 can incorporate any number of devices, tools, or accessories used to perform surgery on a patient 6. For example, the system 1 may include one or more surgical tools (instruments) 7 used to perform surgery (surgical procedure). A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an aspect, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. For example, when manually controlled an operator may (e.g., physically) hold a portion of the tool (e.g., a handle), and may manually control the tool by moving the handle and/or pressing one or more input controls (e.g., buttons) on the (e.g., handle of the) tool. In another aspect, when controlled robotically, the surgical system may manipulate the surgical tool based user input (e.g., received via the user console 2, as described herein).

Generally, a remote operator 9, such as a surgeon or other operator, may use the user console 2 to remotely manipulate the arms 4 and/or the attached surgical tools 7, e.g., during a teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may include one or more components, such as a seat 10, one or more foot-operated controls (or foot pedals) 13, one or more (handheld) user-input devices (UIDs) 14, and at least one display 15. The display is configured to display, for example, a view of the surgical site inside the patient 6. The display may be configured to display image data (e.g., still images and/or video). In one aspect, the display may be any type of display, such as a liquid crystal display (LCD), a light-emitting diode (LED) display, an organic LED (OLED) display, etc. In some aspects, the display may be a 3D immersive display that is for displaying 3D (surgical) presentations. For instance, during a surgical procedure one or more endoscopic cameras may be capturing image data of a surgical site, which the display presents to the user in 3D. In one aspect, the 3D display may be an autostereoscopic display that provides 3D perception to the user without the need for special glasses. As another example, the 3D display may be a stereoscopic display that provides 3D perception with the use of glasses (e.g., via active shutter or polarized).

In another aspect, the display 15 may be configured to display at last one graphical user interface (GUI) that may provide informative and/or interactive content, to thereby assist a user in performing a surgical procedure with one or more instruments in the surgical system 1. For example, some of the content displayed may include image data captured by one or more endoscopic cameras, as described herein. In another aspect, the GUI may include selectable UI items, which when manipulated by the user may cause the system to perform one or more operations. For instance, the GUI may include a UI item as interactive content to switch control between robotic arms. In one aspect, to interact with the GUI, the system may include input devices, such as a keyboard, a mouse, etc. In another aspect, the user may interact with the GUI using the UID 14. For instance, the user may manipulate the UID to navigate through the GUI, (e.g., with a cursor), and to make a selection may hover the cursor over a UI item and manipulate the UID (e.g., selecting a control or button). In some aspects, the display may be a touch-sensitive display screen. In this case, the user may perform a selection by navigating and selecting through touching the display. In some aspects, any method may be used to navigate and/or select a UI item.

As shown, the remote operator 9 is sitting in the seat 10 and viewing the user display 15 while manipulating a foot-operated control 13 and a handheld UID 14 in order to remotely control one or more of the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the system 1 are in a stowed configuration or withdrawn configuration (to facilitate access to the surgical site.) Once access is completed, initial positioning or preparation of the system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one aspect, the remote operator 9 holds and moves the UID 14 to provide an input command to drive (move) one or more robotic arm actuators 17 (or driving mechanism) in the system 1 for teleoperation. The UID 14 may be communicatively coupled to the rest of the system 1, e.g., via a console computer system 16 (or host). The UID 14 can generate spatial state signals corresponding to movement of the UID 14, e.g. position and orientation of the handheld housing of the UID, and the spatial state signals may be input signals to control motions of the robotic arm actuators 17. The system 1 may use control signals derived from the spatial state signals, to control proportional motion of the actuators 17. In one aspect, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the system 1. The system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable one of a variety of wireless data communication protocols, such as BLUETOOTH protocol. Any wired connections may be optionally built into the floor and/or walls or ceiling of the operating room. The system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
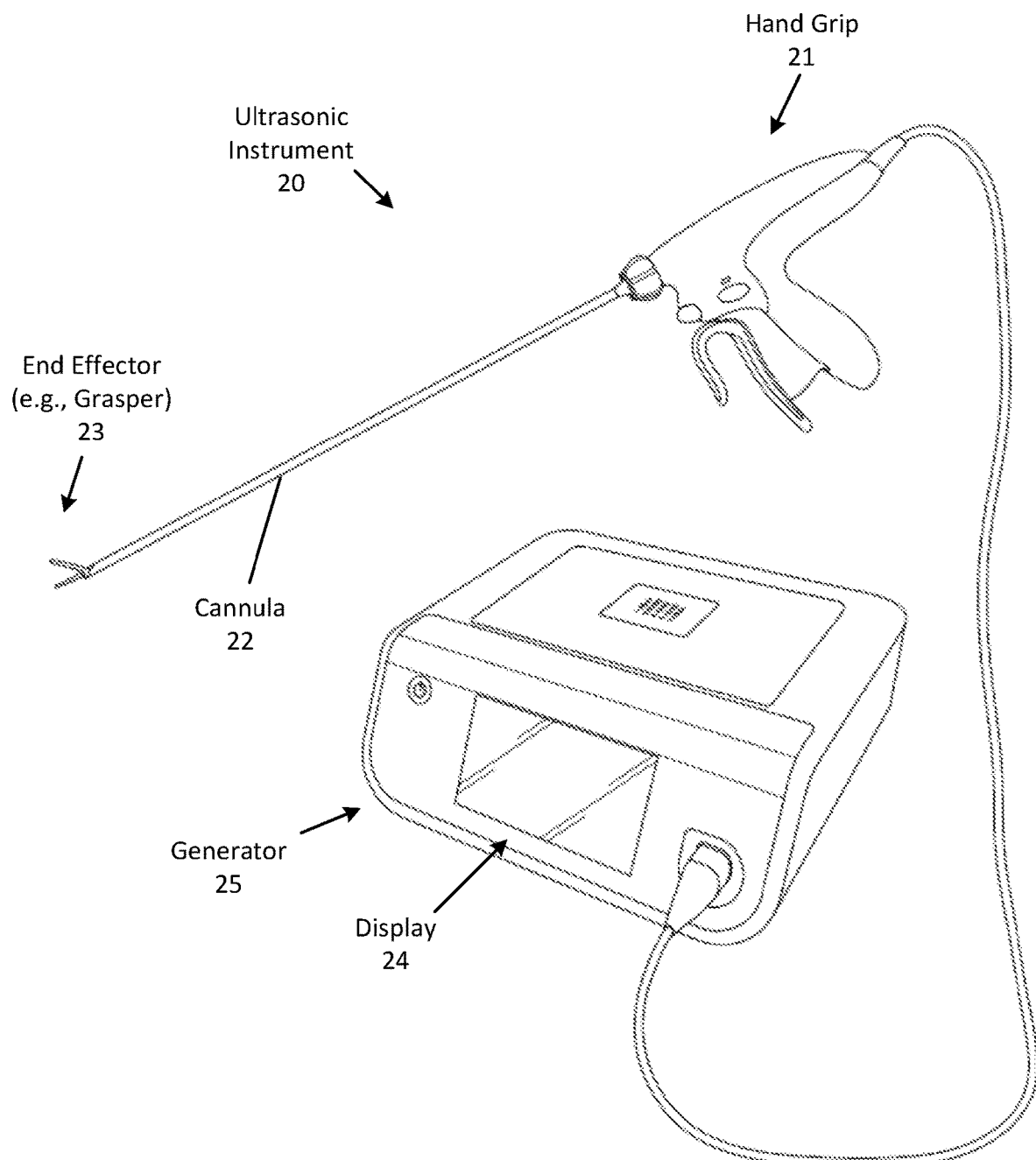
FIG. 2 shows a pictorial view of an ultrasonic instrument and a generator according to one aspect of the disclosure.

FIG. 2 shows a pictorial view of an ultrasonic instrument 20 and a generator 25 according to one aspect of the disclosure. As shown, the ultrasonic instrument is a handheld laparoscopic tool that is configured to perform ultrasonic surgical operations (e.g., cutting and sealing tissue)

based on manual operations (e.g., of the hand grip 21) of the instrument by an operator (e.g., surgeon). The ultrasonic instrument is coupled (e.g., via a cable) to the generator that enables the ultrasonic instrument to operate in one or more power states, as described herein.

The ultrasonic instrument includes a hand grip (e.g., which includes a tool drive) 21, a cannula 22, and an end effector 23 (e.g., which may be coupled to a shaft of the instrument) that is loaded into the cannula, in accordance with aspects of the subject technology.

The hand grip 21 is arranged to be held by an operator, and allows the operator to manipulate the (e.g., end effector 23 of the) ultrasonic instrument during a surgical operation. In one embodiment, the hand grip may include one or more inputs (e.g., a trigger, one or more buttons, etc.), that allow an operator to control the ultrasonic instrument. For example, the instrument may include a trigger that produces a control signal in response to user input by pulling the trigger with one or more fingers while holding the hand grip. In one embodiment, the trigger may be arranged to manipulate the end effector (e.g., by adjusting the position of the hinged arm 31 shown in FIG. 3). In another embodiment, the hand grip may include one or more inputs for changing the power state of the instrument.

As described herein, the hand grip may include a tool drive that is arranged to drive the end effector 23 of the ultrasonic instrument. Specifically, the tool drive may include a (e.g., linear) motor or actuator that is arranged to vibrate (or oscillate) the end effector at one or more frequencies (e.g., at a very high (ultrasonic) frequency, and at a low frequency). In some aspects, the tool drive is configured to vibrate the end effector such that a portion of the end effector (e.g., a blade) moves back and forth along one or more axes. Specifically, the tool drive may vibrate the end effector over one or more excursions, where over each excursion the end effector may be displaced at a different distance from a starting (or beginning) position. More about how the end effector vibrates is described herein. In another aspect, the tool drive may include an ultrasonic transducer that is configured to vibrate the end effector according to an input voltage/input current (e.g., applied by the generator 25).

As described thus far, the ultrasonic instrument may include the end effector 23 and the tool drive 21. In one aspect, the ultrasonic instrument may be separate from (and removeably coupled to) the tool drive. In which case, the ultrasonic instrument as referred herein may be the end effector, which may be coupled to the (e.g., tool drive via the cannula of the) hand grip. Specifically, the cannula may be coupled to the hand grip, where the cannula receives and guides (e.g., a shaft of) the ultrasonic instrument in order to couple to the instrument. By being separate from the hand grip, this may allow multiple different tools to be coupled to the hand grip. In this case, the cannula 22 may receive and guide one or more surgical instruments, such as endoscopes, staplers, etc.

As described herein, the surgical system 1 includes the ultrasonic instrument 20 that is configured to produce heat based on vibrations of its end effector 23. In another embodiment, the instrument may be any type of energy (e.g., laparoscopic) tool that is designed to generate heat.

As described thus far, the ultrasonic instrument 20 may be a hand-held laparoscopic instrument that may be manually is held and manipulated by an operator. In another embodiment, the instrument may be a part of a surgical robotic arm. Specifically, the ultrasonic instrument may be coupled to a robotic arm and powered by the generator, as described herein. For example, the ultrasonic instrument may be coupled to a distal end of a robotic arm (e.g., arm 4 in FIG. 1), which includes several components that allow the robotic arm to be controlled by an operator. For example, the surgical robotic arm 104 may include a plurality of links and a plurality of actuated joint modules for actuating the plurality of links relative to one another. The joint modules may include various types, such as a pitch joint or a roll joint, which may substantially constrain the movement of the adjacent links around certain axes relative to others. The plurality of the joint modules of the robotic arm 104 can be actuated to position and orient the ultrasonic instrument for robotic surgeries. In one embodiment, the ultrasonic instrument may be coupled to the distal end via a tool drive that is arranged to actuate the end effector 23 of the instrument.

In the case in which the ultrasonic instrument is coupled to a robotic arm, movement and operation of the ultrasonic instrument may be performed via one or more user controls (e.g., UIDs, foot pedals, etc.) that are coupled to the surgical system. For example, a UID may be arranged to open/close the grasper 23 of the ultrasonic instrument, and/or may be arranged to adjust a spatial position (in space) of the grasper based on user input (e.g., the position of the UID).

Figure 3:
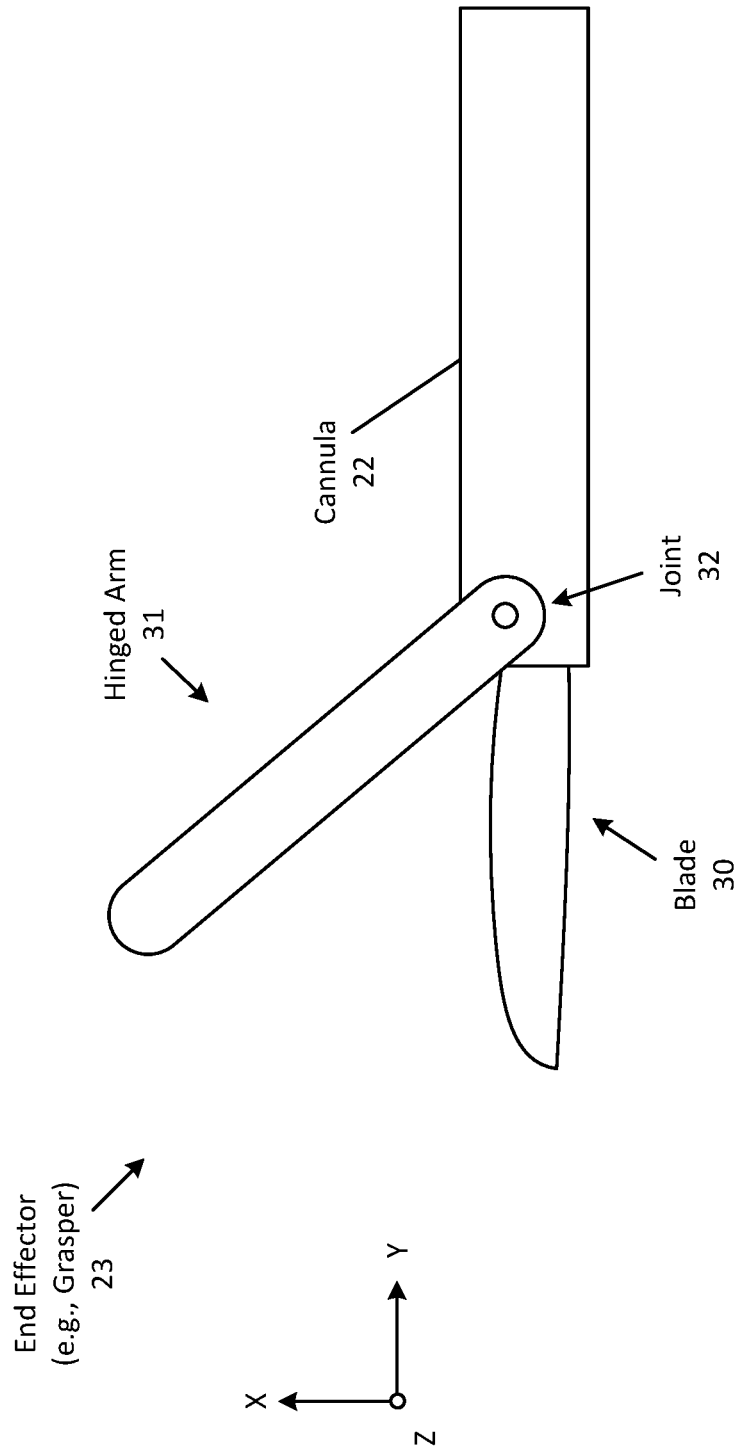
FIG. 3 shows an end effector of the ultrasonic instrument of FIG. 2.

Turning to FIG. 3, this figure shows the end effector 23 of the ultrasonic instrument of FIG. 2. Specifically, this figure shows that the end effector is a grasper (or grasping device) that is received through the cannula 22, and includes a blade 30 (e.g., as one jaw) and a hinged arm (or jaw) 31 that is rotatably coupled to a joint (or robotic wrist) 32. In particular, the blade is received (and extend) through the cannula and is arranged to couple to the tool drive (e.g., of the hand grip 21), such that the blade vibrates back and further within the cannula. The hinged arm 31 is rotatably coupled (at the joint 32) to the cannula 22, and is arranged to rotate. The grasper is arranged to open and close based on the rotational position of the hinged arm about a rotational axis (e.g., the Z-axis) of the joint with respect to the blade (and/or cannula). For example, the grasper is arranged to open (or is in an opened position) when the hinged arm is rotated away from the blade (e.g., by a threshold distance). While in this position, the end effector may be orientated whereby an object, such as tissue, may be disposed between the blade and the hinged arm (e.g., by moving the end effector about the object). The grasper may be closed (or in a closed position), when the hinged arm rotates towards the blade (e.g., within the threshold distance), whereby the grasper may grab the object between the blade and the hinged arm. As described herein, the hinged arm may be arranged to apply pressure against a grasped object (e.g., squeezing the object between the jaws) in order to grab and/or perform a dissection upon the object.

As described herein, the blade 30 is a jaw of the grasper. In particular, the blade is a jaw that may not rotate (e.g., about the Z-axis) with respect to the end effector. The blade may be arranged to vibrate along a longitudinal axis (e.g., the Y-axis) of the blade to produce heat while the ultrasonic instrument is in a high-power state (or mode). In particular, the blade may be driven (e.g., by the tool drive of the hand grip 21) to move back and forth (e.g., linearly) along the longitudinal axis of the end effector (and through the cannula, as described herein), so as to repeatedly displace the blade 30 at a (e.g., constant) frequency. Specifically, the blade may vibrate (e.g., reciprocate back and forth) over an excursion (or displacement) in which the blade moves a distance (e.g., forward or away from the end effector) from a starting position, and then moves the distance back. In one aspect, the excursion may be a distance the blade moves from a starting position to an extended position. In another aspect, the excursion may be the distance the blade moves forward and backward.

As described herein, the blade may produce frictional heat while vibrating against an object. Specifically, the blade may come into contact with tissue while the grasper is squeezing the tissue between the two jaws, and may vibrate against the tissue. As the blade vibrates, the end effector may cut and/or cauterize the tissue, as described herein. In one aspect, the blade may vibrate differently (e.g., over different excursions) based on a power state of (e.g., how much power is being provided to) the ultrasonic instrument. More about the vibrating blade and the power states of the ultrasonic instrument are described herein.

Turning back to FIG. 2, the generator 25 is configured to control and provide power to ultrasonic instrument to control (e.g., heat) the end effector 23 while the instrument is coupled to the generator and being used by an operator (e.g., during a laparoscopic surgery to manipulate tissue and/or perform one or more surgical tasks upon tissue, such as to cut and seal vessels and/or to cut, grasp, and dissect tissues). In particular, the generator may provide power to the ultrasonic instrument, such that the (e.g., ultrasonic instrument of the) surgical system 1 may operate in one of one or more power states. For example, the generator may provide power to the instrument such that the ultrasonic instrument is in a "high-power" state (or "heating cycle") in which the instrument draws power (or current) from the generator (e.g., at a particular voltage) to cause the end effector 23 to produce heat. For example, the generator may provide (e.g., a first) current (or input current) to the (e.g., tool drive of the) hand grip of the ultrasonic instrument, which may use this current to drive the blade 30 to vibrate (or oscillate) over a (first) excursion (and at a particular frequency). Frictional heat may be produced by the end effector while the blade of the end effector is vibrating over this excursion up against an object, such as tissue, as described herein. In another aspect, the ultrasonic instrument may be arranged to operate in a "low-power" state (or "cooling cycle") in which the ultrasonic instrument no longer draws the (sufficient or as much) power provided by the generator, while the instrument was in the high-power state, to heat the end effector. Specifically, while in this state, the generator may be configured to provide less power to the ultrasonic instrument than the power provided by the generator while instrument was in the high-power state, such that the end effector does not produce heat (e.g., when in contact with an object). In particular, the generator may provide less current (e.g., a second current) to the ultrasonic instrument than the (first) current provided by the generator while the instrument operates in the high-power state, and as a result, this does not cause the end effector to produce heat (or as much heat as when the ultrasonic instrument is in the high-power state). As a result, the ultrasonic instrument may begin to cool, once it enters the low-power state from the high-power state. Ultimately, if kept in the low-power state, the ultrasonic instrument would drop to (at least) a threshold temperature (e.g., room temperature). In one aspect, the second current may be less than a predefined threshold current. In one aspect, the blade may vibrate at a same frequency in the low-power state as in the high-power state. In another aspect, the blade may vibrate the same within a tolerance frequency range.

As a result, of the lesser current provided to the instrument while in the low-power state, the blade of the end effector may be driven differently by the tool drive 21 than when the instrument is in the high-power state. In particular, the blade may vibrate over a different excursion than over which the blade vibrates while the instrument is in the high-power state. For instance, while in the high-power state, the blade may vibrate over the first (e.g., high) excursion, which may cause the blade to produce heat when pressed against an object, whereas, while in the low-power state, the blade may vibrate over a second (lower) excursion, which may be less than the first excursion (e.g., the blade being displaced less along the longitudinal axis than in the first excursion). In some aspects, the second excursion may be less than a minimum threshold (e.g., at which the blade would produce heat if the blade were to vibrate over the minimum threshold). In one aspect, the end effector may not produce frictional heat, while vibrating over this lower excursion and while up against an object, such as a blood vessel. In one aspect, the resonant frequency is maintained within a tolerance range regardless of which power state the instrument is operating.

In one aspect, the difference in vibration of the end effector may be based on the amount of power that is being drawn by the ultrasonic instrument while in the different states. For instance, the excursion at which the blade is displaced while it oscillates may be based on (e.g., proportional to) the power drawn by the instrument, whereby more power drawn by the instrument may cause the blade to vibrate over the high excursion. Conversely, while the ultrasonic instrument is in the low-power state the instrument may draw less power that causes the blade to vibrate less (than while the instrument is in the low-power state). As a result of oscillating over a lesser displacement, the blade may not produce frictional heat (e.g., while in contact with tissue). In another aspect, the blade may produce some frictional heat while in the low-power state and in contact with an object, but may be less than the heat produced while the instrument is in the high-power state. In this case, this produced frictional heat may not be enough to cut and/or seal tissue. In some aspects, as a result of operating in the low-power state, the end effector of the ultrasonic instrument may enter a cooling cycle, whereby the heat produced by the end effector while the instrument was in the high-power state dissipates (e.g., over a period of time). In another aspect, the blade may not vibrate (e.g., the tool drive 21 may not drive the blade) while in this low-power state.

In one aspect, the system may enter (or operate in) at least one of the power states based on user input (e.g., received by the generator 25). In particular, the generator may provide power to the ultrasonic instrument based on receiving user input into one or more input devices (e.g., input into a foot petal, an UID that is controlled by an operator and communicatively coupled with the system 1, and/or input at the hand grip 21 of the ultrasonic instrument). The provided power based on the user input may put the ultrasonic instrument in the high-power state in which the ultrasonic instrument draws power from the generator to heat the (e.g., blade 30 of the) end effector 23. For example, when the generator receives (a first) user input (e.g., by the operator pulling on or pressing a trigger on the hand grip 21), the generator may provide current to the (e.g., tool drive 21 of the) ultrasonic instrument, which uses the current to drive the end effector, as described herein. Thus, in the case where the trigger controls the hinged arm of the end effector, the generator is configured to provide the current when the hinged arm is moved (e.g., towards the blade 30 by at least a threshold distance). In another aspect, the system may enter the low-power state based on another (e.g., second) user input (e.g., receiving input from a different input device coupled to the generator, such as a foot pedal).

In some aspects, the ultrasonic instrument may be arranged to switch between the high-power state and the low-power state. As described herein, the instrument may operate in the high-power state while the generator is receiving user input (e.g., the user pulling on or pressing a trigger on the hand grip). The instrument may operate in the low-power state in response to the generator not receiving user input. For instance, the ultrasonic instrument may switch from the high-power state into the low-power state in response to the user releasing the trigger on the hand grip, the generator may transition between the two states). In one aspect, the instrument may operate in the low-power state while the operator is not actively using the instrument to perform ultrasonic instrument operations, as described herein. Specifically, the system may enter the low-power state, while user input is not received into one or more input devices that are used by the operator to enter the high-power state. Once, however, the operator wishes to actively use the ultrasonic instrument, the ultrasonic instrument may switch back into the high-power state (e.g., in response to user input). In another aspect, the instrument may operate in the low-power state in response to receiving user input (e.g., the user pressing a button on a UID). In another aspect, the instrument may operate in this state for a period of time. As described herein, the surgical system is configured to determine a temperature of the end effector while in the low-power state (e.g., after switching from the high-power state) in order to notify an operator of the temperature, which may be high due to the instrumenting having operated in the high-power state. Once the end effector cools to a particular temperature (e.g., equal to or below a predefined temperature), the generator may deactivate the instrument by ceasing to provide the lower current, since at this temperature the end effector may not cause thermal injuries if it were to come into contact with tissue.

In one aspect, the generator may provide different levels of current to heat up the blade, which may be based on user input. For instance, the generator may receive a first user input (e.g., from one petal coupled to the generator) and, in response, provide the ultrasonic instrument with a maximum (allowable) amount of current. The ultrasonic instrument may then drive the end effector over a maximum (e.g., predefined) excursion, which may result in the end effector producing heat at a (first) high temperature. When the generator receives a second user input (e.g., from another petal coupled to the generator), however, the generator may provide a lesser amount of current to the ultrasonic instrument. As a result, the ultrasonic instrument may draw less power to cause the end effector to vibrate over a (second) lower excursion, which may be lower than the first excursion over which the blade vibrates in response to the first user input. This lower excursion, however, may cause the end effector to heat at a lower temperature than the first temperature of the end effector when the ultrasonic instrument draws more current (in response to the generator receiving the first user input). By heating the end effector to different temperatures, different types of tissues may be cut and/or cauterized. For example, fattier tissues may require the end effector to be hotter (having the first temperature), whereas thinner (and less fatty) tissues may require less heat (having the second temperature), in order to cut and/or cauterize the tissues. In another aspect, the generator may be configured to provide one current while in the high-power state (e.g., to drive the end effector over the first high excursion).

As described herein, the ultrasonic instrument may be activated (e.g., operate in the high-power state) based on whether the end effector is in a closed position so as to grasp an object (e.g., a piece of tissue). For example, the ultrasonic instrument may be (e.g., user) activated, such that the ultrasonic instrument may operate in the high-power state so as to draw enough current to cause the end effector to produce heat. In particular, the generator may activate the ultrasonic instrument upon receiving user input to close the end effector (e.g., to cause the hinged arm 31 to move within a distance of the blade 30). Once user input is received to move the hinged arm, the generator may be configured to provide (e.g., enough) power to activate the instrument, as described herein. In some aspects, the generator may activate the instrument based upon a determination that the hinged arm and/or the blade are in contact with an object. For instance, the ultrasonic instrument may include one or more sensors (e.g., force sensors), that detect a presence of an object and/or detect that an object is in contact with both arms. Upon making this determination, the generator may provide the first current to oscillate the blade in order to cause the blade to produce heat.

In one aspect, the (e.g., generator of the) surgical system may be configured to determine one or more characteristics of the ultrasonic instrument, while the instrument is in one or more power states. For example, the generator may be configured to keep track (or monitor) characteristics, such as an input voltage, an input current, a resonance state, and/or a resonance frequency of the ultrasonic instrument. In one aspect, the generator may be configured to monitor at least some of these characteristics of the instrument, while the instrument operates in the high-power states. Unlike conventional systems, however, that are unable to determine characteristics while an ultrasonic instrument is in the cooling cycle because the instrument is deactivated (e.g., no power being provided by the generator), the surgical system of the present disclosure is able to determine the characteristics while the instrument is in the low-power state (or cooling cycle) due to the instrument drawing at least some power. For example, the generator may determine the resonance frequency of the (e.g., blade 30 of the) end effector, while in the low-power state.

In one aspect, the surgical system may include additional components. For example, the system may include a cable that connects the generator to the ultrasonic instrument (e.g., the ultrasonic transducer, which is configured to convert an electric current drive signal to mechanical vibrations). In one aspect, the ultrasonic transducer may be connected to a waveguide, which is connected to the blade 30 of the end effector 23.

Also shown, the generator 25 also includes a display 24, which is arranged to disclose information regarding the operation of the ultrasonic instrument. For instance, the display may present temperature information, which state the ultrasonic instrument is currently in, and one or more of the characteristics described herein.

Figure 4:
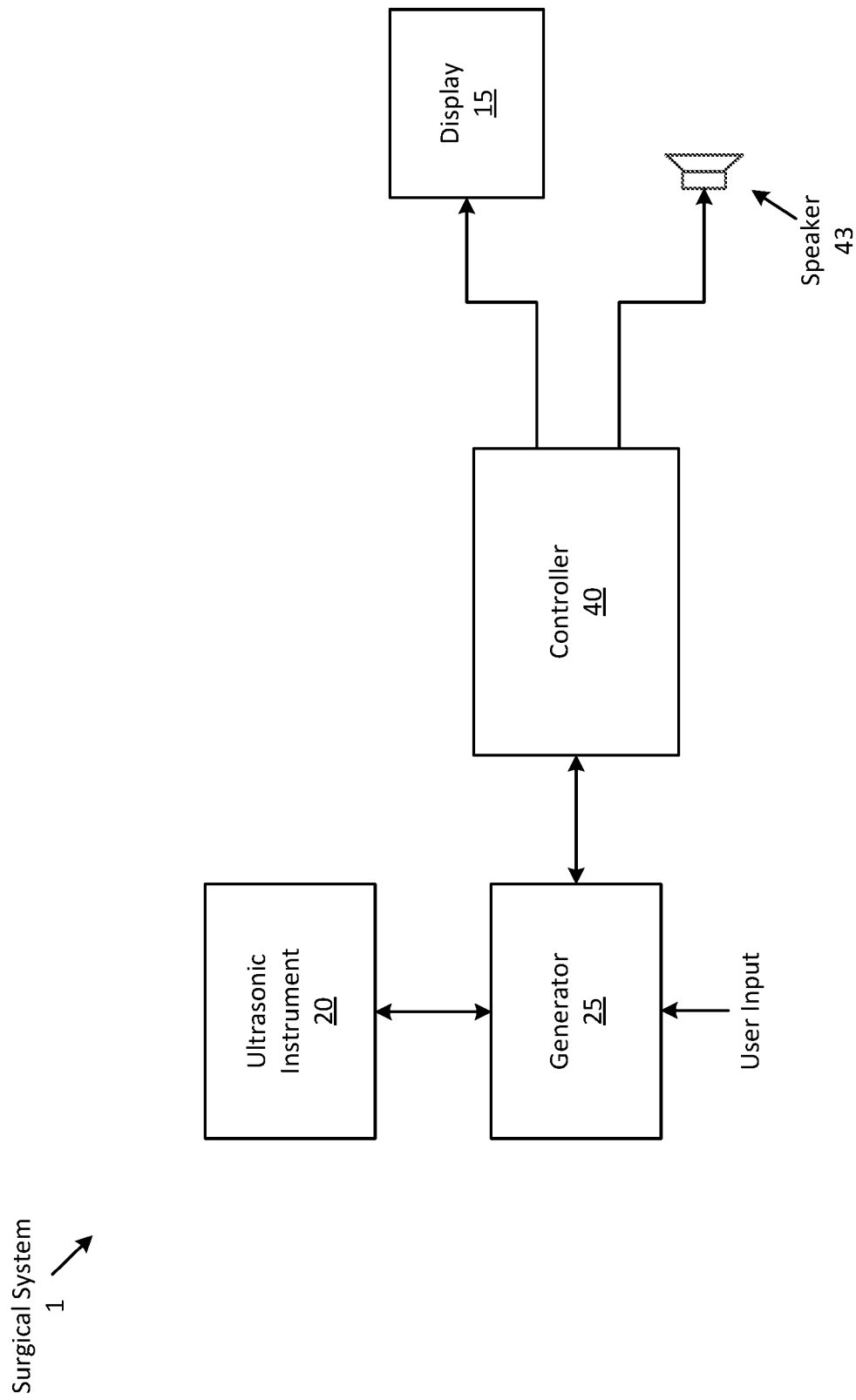
FIG. 4 is a block diagram of the surgical system according to one aspect.

FIG. 4 is a block diagram of the surgical system 1 according to one aspect. The system includes the ultrasonic instrument 20, the generator 25, a controller 40, the display 15, and a speaker 43 (that may be a stand-alone speaker or a part of an electronic device of the system, such as the user console 2). In one aspect, the system may include more or less elements, such as having more than one display and/or not having the speaker.

In some aspects, controller 40 may be a special-purpose processor such as an application-specific integrated circuit (ASIC), a general purpose microprocessor, a field-programmable gate array (FPGA), a digital signal controller, or a set of hardware logic structures (e.g., filters, arithmetic logic units, and dedicated state machines). In one aspect, the controller may be a part an electronic device, such as the console computer system 16, the control tower 3, and/or the user console 2. Although illustrated as being a single component, in one aspect the controller may comprise one or more electronic components (e.g., processors, memory, etc.) that are communicatively coupled on a single electronic device (such as the console computer 16), or across multiple devices (e.g., communicating over a wireless computer network). In some aspects, the controller may be a part of a separate device, such as a part of a remote server that is in communication with one or more electronic devices. In another aspect, the controller may be a part (e.g., at least partially integrated within) the generator 25. In which case, at least some of the other elements (e.g., the speaker and display) may also be a part of (integrated within) the generator. As a result, at least some of the operations performed by the controller described herein may be performed by the generator.

As described herein, the controller is configured to perform temperature estimation operations for the surgical system 1 to determine a (e.g., real-time) temperature of the (e.g., end effector of the) ultrasonic instrument, while the instrument is in the low-power state (e.g., not being actively heated in order to cut and/or seal tissue). Specifically, the controller may determine the temperature based on one or more characteristics of the ultrasonic instrument that are determined while in the low-power state, such as a resonance frequency of the (e.g., blade of the) end effector. At least some of the operations performed by the controller may be implemented in software (e.g., as instructions) stored in memory of the surgical system (and/or stored in memory of the controller) and executed by the controller and/or may be implemented by hardware logic structures. In one aspect, at least some of the operations performed by the controller may be performed each time the instrument enters the low-power state.

As shown, the generator may receive user input (e.g., via one or more electronic devices coupled to the generator) for causing the generator to perform one or more operations. For instance, the user input may be received via the ultrasonic instrument (e.g., when the user pulls on a trigger of the hand grip) in order to cause the generator to provide current that causes the ultrasonic instrument to switch from the low-power state to the high-power state, as described herein.

Figure 5:
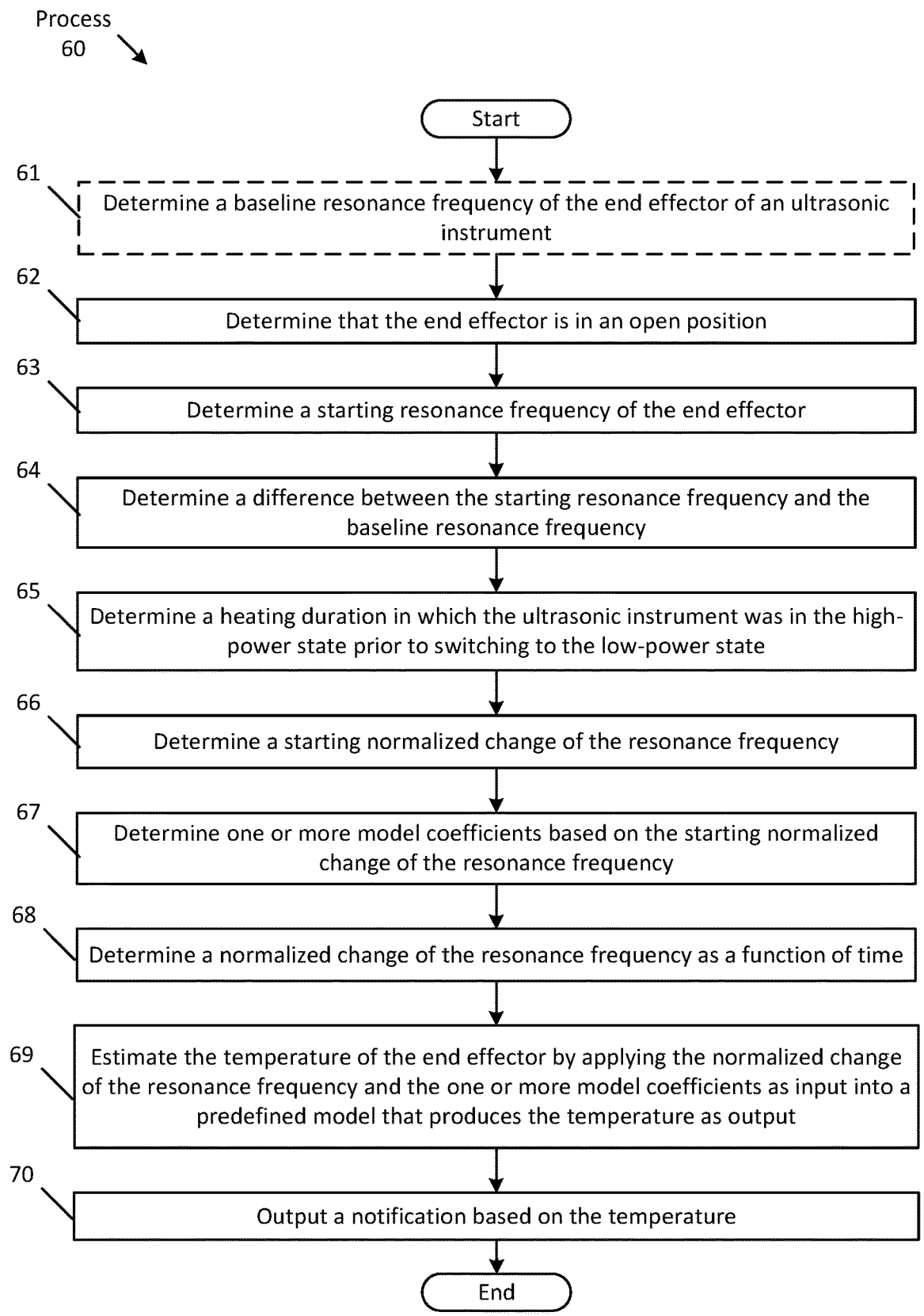
FIG. 5 is a flowchart of a process for determining a temperature of the end effector of the ultrasonic instrument that is in a low-power state.

FIG. 5 is a flowchart of a process 60 for determining a temperature of the end effector of the ultrasonic instrument that is in a low-power state. In particular, at least some of these operations may be performed once and/or while the ultrasonic instrument is in the low-power state. For example, the operations may be performed (e.g., each time) the ultrasonic instrument switches from the high-power state to the low-power state, which may be based on user input, as described herein. In which case, the surgical system may perform these operations to estimate and output (e.g., display) the temperature of the ultrasonic instrument in real-time to the operator of the instrument. In one aspect, the process may be performed by the surgical system 1. For instance, each of the processes may be performed by the controller 40. As another example, at least some operations may be performed (e.g., by one or more processors of) the generator 25. Thus, this figure will be described with reference to FIG. 4.

The process begins by the controller determining a baseline (or initial) resonance frequency of the end effector of the ultrasonic instrument 20 (at block 61). For instance, the controller may determine baseline resonance frequency of the blade 30 of the end effector at an initial time, $t_0$, as $RF(t_0)$. In one aspect, the controller may determine this baseline resonance frequency when the ultrasonic instrument 20 is coupled (e.g., plugged into) the generator 25. For instance, once the instrument is plugged into the generator, the generator may perform one or more diagnostic operations upon the instrument. Based on those operations, the generator may determine the baseline resonance frequency of the end effector's blade, and provide the frequency to the controller. In some aspects, the generator determines the resonance frequency electronically. For example, the generator may sense voltage and current waveforms (and the difference in phase angle between the two waveforms) that are used to drive the blade of the end effector. Specifically, the ultrasonic instrument 20 (e.g., the tool drive) may include an ultrasonic transducer that is configured to vibrate the blade according to the input voltage and current waveforms. The frequency that produces a difference in phase angle of a threshold (e.g., zero) is the resonance frequency. In one aspect, the generator continues to drive the ultrasonic transducer in resonance and may adjust the output voltage (which may be called phase lock) to continue to drive in resonance (as resonance frequency changes with changes in temperature). In another aspect, the controller 40 may adjust the output frequency. In another aspect, other known methods may be used to determine the resonance frequency.

In some aspects, this baseline frequency may be determined while the end effector is at (or approximately) room temperature (e.g., a temperature between 20-25° C.). In another aspect, the baseline frequency may be determined once and stored in memory of (e.g., the controller 25 of) the surgical system 1. For instance, the baseline frequency may be determined a first time the instrument is coupled to the generator. In another aspect, the baseline resonance frequency may be determined every time the ultrasonic instrument is plugged into the generator. In another aspect, the baseline frequency may be determined at start up (e.g., during initial powering up) of the (e.g., ultrasonic instrument by the) surgical system.

In one aspect, the operations performed in this block may be omitted from the process 60. For example, as described herein, at least some of these operations may be performed each time the ultrasonic instrument enters the low-power state. The determination of the baseline frequency, however, may be performed one time (e.g., during the initial powering up), in some aspects. As a result, the process 60 may omit this operation in subsequent (at least partial) performances of this process.

The controller 40 is configured to determine that the end effector is in an open position, while the ultrasonic instrument is in the low-power state (at block 62). Specifically, the controller may determine that the grasper 23 is in an open position in which the hinged arm 31 is rotated away (e.g., at a threshold rotational distance) from the blade 30. For instance, the controller may determine that the ultrasonic instrument has received user input (e.g., from the generator) to move the hinged arm 31 away from the blade 30. Specifically, the generator may provide the controller with an indication of the position of the hinged arm with respect to the blade, and the controller may determine whether the end effector is open based on whether a distance between both arms is equal to or above the threshold distance. In another aspect, the generator may provide the controller the end effector's status based on the position of the hinged arm (e.g., whether the end effector is in an open or closed position). In another aspect, the controller may determine that the end effector is in the open position using one or more signal processing operations based on one or more characteristics of the end effector. For instance, the controller may receive the characteristics from the generator, such as a resonance frequency of the end effector, and determine whether the end effector is open based on the resonance frequency. In one aspect, this determination may be based on performing signal processing operations upon a first derivative of the resonance frequency.

The controller determines a starting (or an initial) resonance frequency of the end effector (at block 63). Specifically, this may be a starting resonance frequency that is determined by the surgical system once (or in response to) the end effector of the instrument is in the open position (while also operating in the low-power state). In one aspect, controller may determine this starting resonance frequency of the blade 30, after (e.g., immediately or within a period of time when) the controller determines that the end effector is in the open position, as SRF. In one aspect, this starting frequency may be measured and provided by the generator, as describe herein. The controller determines a difference between the starting resonance frequency and the baseline resonance frequency (at block 64). In particular, the controller determines the difference as, $$\Delta SRF = SRF - RF(t_0)$$

In one aspect, the difference, $\Delta SRF$, represents the resonance frequency drift from (or change between) the baseline (or nominal) resonance frequency to the starting resonance frequency of the blade. The controller 40 determines a heating duration in which the ultrasonic instrument was in the high-power state prior to switching to the low-power state (at block 65). Specifically, the controller is determining an amount of time at which the ultrasonic instrument was active (e.g., in the high-power state) before operating in its current low-power state. This heating duration (HD) may be expressed as $$HD = t_{heating\ end} - t_{heating\ start}$$

In this expression $t_{heating\ end}$ represents a time at which the ultrasonic instrument switched to the low-power state and $t_{heating\ start}$ is another time when the ultrasonic instrument entered the last high-power state. In one aspect, $t_{heating\ start}$ is a time that is previous to $t_{heating\ end}$.

The controller determines a starting (an initial) normalized change of the resonance frequency (at block 66). Specifically, this normalized change in frequency may be the average drift rate of the resonance frequency at the start of when the ultrasonic instrument entered the low-power state (e.g., and began its cooling cycle due to the ultrasonic instrument not drawing sufficient power to heat its end effector), as $$\Delta SRF_{NORM} = \frac{\Delta RF}{HD}$$

The controller determines one or more model coefficients based on the starting normalized change of the resonance frequency (at block 67). In one aspect, each of the coefficients may be determined based on the normalized change in resonance frequency (e.g., determined at block 66). In one aspect, the number of coefficients determined may be based on the particular model that may be used by the controller to determine the temperature of the end effector. For example, when the model is a third-order cooling polynomial model, the determined coefficients may include four coefficients (A, B, C, D), as $$A = C_{11}*\Delta SRF_{NORM} + C_{12}$$

$$B = C_{21}*\Delta SRF_{NORM} + C_{22}$$

$$C = C_{31}*\Delta SRF_{NORM} + C_{32}$$

$$D = C_{41}*\Delta SRF_{NORM} + C_{42}$$

In one aspect, the eight constants, $C_{11}$ through $C_{42}$ may be predefined in a controlled environment (e.g., a laboratory). For example, the constants may be defined by fitting "normalized starting resonance frequency" data into third-order polynomials that are observed during modeling on one or more tissues using one or more ultrasonic instruments. For instance, a temperature sensor (e.g., a pyrometer) may be used to measure the end effector's temperature during one or more heating cycles and one or more cooling cycles of the end effector. During these measures one or more characteristics of the ultrasonic instrument, as described herein, may be determined (e.g., by the generator). For example, first, the end effector is in a closed position to grasp a piece of tissue. Then, the ultrasonic instrument may be (e.g., user) activated, such that the instrument is in the high-power state for a controlled period of time (e.g., one second, etc.). Afterwards, the instrument is switched (e.g., the generator is switched) to the low-power state to end the heating cycle, the end effector is put in the open position, and the tissue is taken off the jaws of the end effector (e.g., the end effector may be moved away from the tissue). In one aspect, the cooling cycle may begin once the end effector is moved away from the tissue (e.g., such that tissue is no longer in contact with the jaws of the grasper). In one aspect, depending on the grasped tissue type/thickness and the activation during the heating cycle, the peak temperature of the end effector (while the instrument is in high-power state) will vary. The resonance frequency, the temperature data of the ultrasonic instrument, and/or the duration of the heating cycle may be determined during the cooling cycle, and may be used to determine one or more of the constants. In some aspects, the determined constants may be different based on the ultrasonic instrument that is being used with the surgical system. In which case, the controller may be configured to determine the type of ultrasonic instrument is coupled to the surgical system, and may be configured to determine one or more of the constants based on the determined type.

As described herein, the model may be a third-order cooling polynomial model that includes four coefficients. In another aspect, the model may be a second-order polynomial model. In which case, the model may include the same or a different number of coefficients.

The controller 40 determines a normalized change of the resonance frequency as a function of time (at block 68). Specifically, after determining the starting resonance frequency, the controller may continue to determine the resonance frequency of the end effector. For example, the generator may provide one or more measured resonance frequencies of the blade of the end effector after the starting frequency. In one aspect, the controller may receive one or more (subsequent) measured resonance frequencies (e.g., every millisecond, second, minute, etc.). The controller may determine, for each determined resonance frequency, RF, a drift from the baseline frequency as $$\Delta RF = RF - RF(t_0)$$

The controller may determine the normalized changes to all (or at least some) determined frequencies (e.g., where one or more of the resonance frequencies were determined after the starting resonance frequency) as a function of time, which may be defined as $$\Delta RF_{NORM}(t) = \frac{\Delta RF(t)}{HD}$$

In one aspect, this function may be determined from one or more of the determined resonance frequencies. The controller 40 may estimate (or determine) the temperature of the end effector by applying the normalized change of the resonance frequency and the one or more model coefficients as input into a predefined model that produces the temperature as output (at block 69). In particular, the controller may define the temperature as the following third-order polynomial model, which is a function of time $$T(t)=A*(\Delta RF_{NORM}(t))^3 B*(\Delta RF_{NORM}(t))^2 C* \Delta RF_{NORM}(t)D$$

Therefore, the controller may determine the temperature (e.g., at any given time) of the blade of the end effector based on changes to determined resonance frequencies of the blade. Thus, by performing one or more of the temperature estimation operations described herein, the controller is able to determine (estimate) the temperature of the end effector based on one or more characteristics (e.g., the resonance frequency) of the ultrasonic instrument, without using (e.g., data from) a temperature sensor. In one aspect, the ultrasonic instrument may not include a temperature sensor.

The controller 40 is configured to output a notification based on the temperature (at block 70). For example, the controller may display a (e.g., pop-up) notification that includes the temperature of the end effector on the display 15 of the surgical system 1. In which case, the displayed notification may be a graphical user interface (GUI) item that is overlaid on video and/or images that are being displayed on the display, such an endoscopic video, which may be provided by an endoscopic camera that has a field of view of a surgical site (e.g., within an abdomen of a patient). In another aspect, the notification may indicate a status (e.g., "Hot") of the end effector. In another aspect, the system may output an audible notification through the speaker 43. For instance, the audible notification may be one or more sounds (e.g., a beep), which indicates that the end effector has a temperature that is above a threshold. In another aspect, the audible notification may be spoken word (e.g., "Caution! The Blade is Hot!"). In another aspect, any type of notification may be used.

In one aspect, the controller may perform one or more of these operations in real-time, such that the surgical system may (e.g., continuously) estimate and provide the temperature to the operator of the surgical system (e.g., while the ultrasonic instrument is in the low-power state). In which case, the controller may continue to display the temperature of the end effector, while the ultrasonic instrument is cooling down. In some aspects, the system may cease providing the notification upon the temperature of the end effector reaching a threshold. For instance, the controller may determine whether the temperature is above a temperature threshold. In response to determining that the temperature is above the threshold, the controller may output the notification. If, however, the temperature was to be below the threshold, the controller may cease outputting the notification, which may provide the operator the indication that the end effector is no longer hot. In another aspect, the controller may output a notification that the end effector is no longer hot (e.g., by displaying a pop-up notification on the display, such as "The Blade is Cool".

In some aspects, the controller may be configured to determine a time at which the temperature of the end effector will be below a temperature threshold. For instance, as described herein, the controller determines the temperature of the end effector based on a polynomial model (or a particular order) that is a function of time. In which case, the controller may use the model to estimate when the blade will be below the temperature threshold based on a rate of change of the temperature with respect to time. In another aspect, the controller may determine the time based on changes to the determined resonance frequencies of the end effector. For instance, the controller may receive one or more resonance frequencies, subsequent to the initial resonance frequency, while the ultrasonic instrument is in the low-power state. The controller may determine the time at which the temperature will be below the temperature threshold based on a rate of change of the subsequent (and initial) resonance frequencies. Once determined, the controller may be configured to include the time with the notification in order to provide the operator an indication as to when the end effector will be cool.

As described thus far, the surgical system is configured to determine the temperature of the ultrasonic instrument in order to output a notification, such as displaying the temperature on a display. This information may be used by the operator of the ultrasonic instrument (e.g., during a surgical procedure) in order to avoid using the instrument to touch surrounding tissue while the blade is still hot. As a result, the operator may use this information to properly regulate how to manipulate the ultrasonic instrument (e.g., being more cautious to avoid contact with tissue). In another aspect, this information may be used by the operator to continue performing ultrasonic surgical operations. For instance, with the end effector retaining residual heat from when the instrument was activated, the operator may continue to use the instrument to perform one or more operations, such as sealing vessels. In which case, the operator may use the displayed temperature to determine whether to continue to use the instrument (e.g., based on whether the temperature of the end effector is hot enough to continue to seal vessels), while the instrument is in the low-power state (e.g., without having to reactive the instrument).

Some aspects may perform one or more variations to the process 60 described herein. For example, the specific operations of the process may not be performed in the exact order shown and described. The specific operations may not be performed in one continuous series of operations and different specific operations may be performed in different aspects. As described herein, the process determines that the end effector is in the open position at block 62. In some aspects, the controller may wait to perform the subsequent operations (e.g., 63-70), until the end effector is in this position. In which case, these operations of the process 60 may be performed a period of time after the ultrasonic instrument switches to the low-power state. This may be due to the operator of the surgical instrument maintaining the end effector in the closed position for the period of time, while the instrument is in the low-power state. In another aspect, at least some of these operations may be performed each time the ultrasonic instrument is activated (e.g., operating in the high-power state). For example, the controller may determine one or more new model coefficients (e.g., at block 67), and consequently a new temperature estimation model is created after each activation of the ultrasonic instrument.

As described herein, the controller is configured to determine one or more model coefficients and to estimate the temperature by applying a normalized change of the resonance frequency and the coefficients into a predefined model. In one aspect, the controller may be configured to determine the model based on the ultrasonic instrument. Specifically, the model may be based on one or more physical characteristics of the instrument, such as the mechanical structure of the instrument's end effector. In some aspects, at least some of these physical characteristics may be different between different ultrasonic instruments (e.g., where blades between instruments are different sizes/shapes). With differences between physical characteristics, models for the instruments may be different. For example, when the model is a polynomial model, the order of the model (e.g., second-order or third-order), may be based on a particular instrument's physical characteristics. In one aspect, the number of model coefficients may also be based on the instrument's characteristics. In which case, the controller may be configured to determine the ultrasonic instrument (of one or more instruments) that is a part of the surgical system (e.g., coupled to the generator 25), and configured to the determine the model (e.g., the order of the polynomial model) that is associated with the determined instrument. In one aspect, this determination may be a table lookup into a data structure (that has a table) that associates different types of ultrasonic instruments with one or more models (and/or model coefficients).

Figure 6:
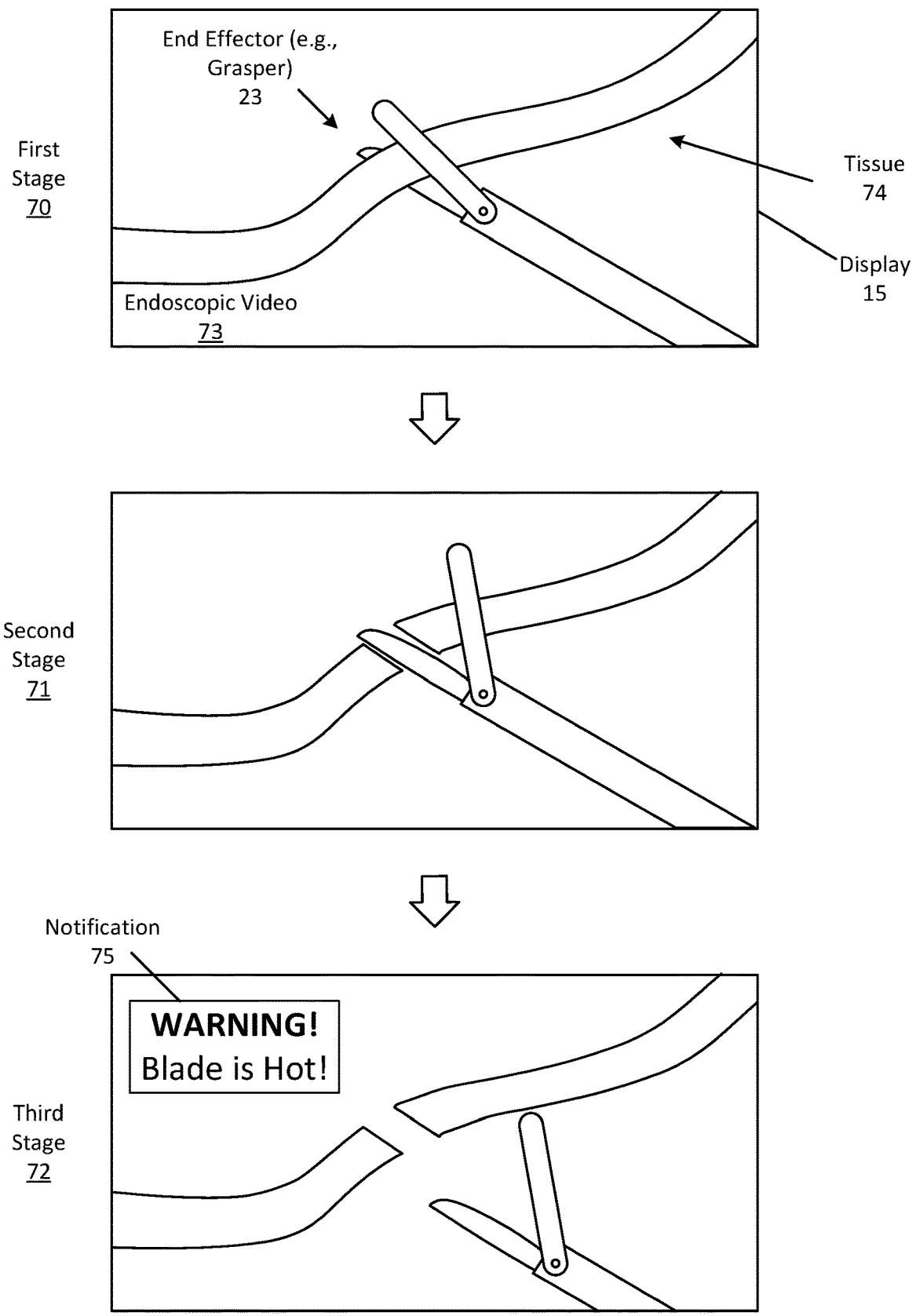
FIG. 6 show several stages of a display of the surgical system that is showing actions performed by the end effector of the ultrasonic instrument and shows a notification based on the determined temperature of the end effector.

FIG. 6 show several stages of a display of the surgical system that is showing actions performed by the end effector of the ultrasonic instrument and is showing a notification based on a determined temperature of the end effector. Specifically, each of the three stages 70-72 is showing the display 15 of the surgical system, which is displaying endoscopic video 73. The video, which may be provided by one or more endoscopic cameras of the system 1, shows a surgical site within a patient to which a surgical procedure is being performed. In particular, the video 73 shows tissue 74 (e.g., a blood vessel) that is being manipulated by the end effector 23. In another aspect, the display may show other content, such as other video content and/or a graphical user interface (GUI) of the surgical system that is displaying one or more UI items.

The first stage 70 shows that the end effector 23 is grasping (a portion of) the tissue 74. In particular, the grasper has been positioned such that the tissue is disposed between the hinged arm 31 and the blade 30, and the hinged arm has been moved towards the blade 30 such that the tissue is sandwiched between (e.g., in contact with) both arms. In addition, the ultrasonic instrument of the end effector 23 is being used to perform ultrasonic instrument operations upon the tissue. Specifically, the ultrasonic instrument may be in the high-power state in which the end effector is vibrating while in contact with the tissue 74, thereby producing frictional heat in order to cut and seal the tissue.

The second stage 71 shows the result of cutting and sealing the tissue with the end effector. As shown, the tissue has been cut into two pieces by the end effector and has also been cauterized. In addition, the grasper is now in the open position (with the hinged arm 31 being moved away from the blade). With the tissue being cut, the operator may no longer need to heat the end effector, and therefore the instrument may switch from the high-power state to the low-power state in order to enter a cooling cycle, as described herein. Thus, in this stage the ultrasonic instrument may be provided current (e.g., by the generator 25) that is below a current threshold at which the instrument causes the blade to produce (e.g., frictional) heat. In addition, the (controller 40 of the) surgical system may estimate, while the current is provided to the instrument, a temperature of the blade based on a resonance frequency of the blade, as describe herein. In one aspect, the controller may perform at least some of the operations described herein in order to estimate the temperature.

The third stage 72 shows that a notification 75 is being displayed, as a graphical user interface (GUI) item that is overlaid on top of the endoscopic video 73. The notification is based on the estimated temperature of the blade. In particular, the notification include text of "WARNING! Blade is Hot!" in order to alert the operator of the temperature state of the blade. In another aspect, the notification may be present separately from (e.g., other) video and/or images that are displayed on the display 15. In one aspect, the surgical system may continue to determine the temperature while the blade and display the notification, while the blade cools. In some aspects, when the blade is equal to or less than a temperature threshold, the surgical system may remove the notification, indicating to the operator that the blade is no longer hot.

As described herein, the display 15 is arranged to present the endoscopic video 73 and the notification. In one embodiment, the generator's display 24 may display the video and/or notification. For example, the display 24 may display the endoscopic video and the notification, or may display the notification, while the display 15 of the system presents the endoscopic video.

Figure 7:
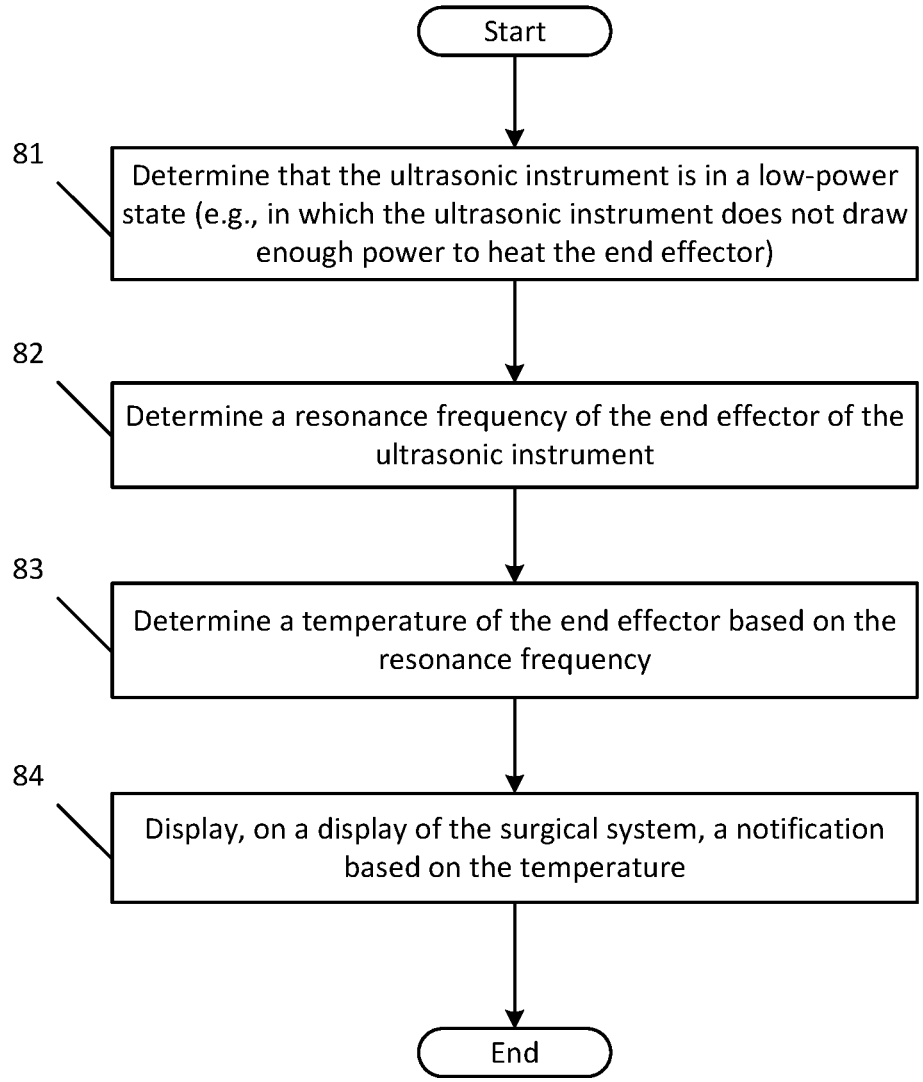
FIG. 7 is a flowchart of a process for an aspect of determining the temperature of the end effector.

FIG. 7 is a flowchart of a process 50 for an aspect of determining the temperature of the end effector. In particular, at least some of the operations in this process may be performed by the controller 40 of the surgical system. In another aspect, at least some of the operations may be performed the generator 25. The process 50 begins by the controller 40 determining that the ultrasonic instrument 20 is in a low power state (at block 81). Specifically, the controller determines that the ultrasonic instrument is not drawing enough (sufficient) power (e.g., is not being provided enough current by the generator 25) to heat the end effector 23 of the ultrasonic instrument (e.g., while the end effector is in contact with tissue). In one embodiment, the controller may receive an indication from the generator that it is providing less power (or is in the low-power state). In another embodiment, the controller may receive an indication that the operator of the surgical system no longer wishes to actively use the instrument (e.g., based on user input) to perform heat-related surgical tasks (e.g., cutting, cauterizing, etc.)

The controller determines a resonance frequency of the end effector (at block 82). The controller determines a temperature of the end effector based on the resonance frequency (at block 83). Specifically, the controller may perform one or more of the operations of process 60 described in FIG. 5 to determine the resonance frequency and the temperature. The controller displays, on a display of the surgical system, a notification based on the temperature (at block 84). For instance, the notification may include the temperature of the end effector and/or may include a textual indication that the blade is hot, as described herein.

Some aspects may perform variations to the processes 60 and/or 80 described herein. For example, the specific operations of at least some of the processes may not be performed in the exact order shown and described. The specific operations may not be performed in one continuous series of operations and different specific operations may be performed in different aspects. For instance, the controller may determine the resonance frequency and the temperature, while the ultrasonic instrument is in the low-power state. In another embodiment, at least some of these operations may be performed after the ultrasonic instrument has been in the high-power state. For instance, the controller may determine that the ultrasonic instrument is in the high power state in which the instrument draws power (e.g., from the generator 25) to heat its end effector 23. For instance, the controller may receive an indication from the generator that it is providing current to the instrument (e.g., based on user input) in order for the instrument to vibrate the end effector over an excursion that results in the production of frictional heat when in contact with an object. Thus, the ultrasonic instrument may be active, allowing the operator of the surgical system to perform one or more ultrasonic instrument operations (e.g., cutting, sealing, etc.). The controller may switch the ultrasonic instrument to the low-power state based on one or more conditions being met, such as receiving an indication that the operator of the surgical system no longer wishes to actively use the instrument (e.g., based on user input). Once the ultrasonic instrument switches to the low-power state, at least some of the operations described herein may be performed to determine and display the temperature of its end effector.

As described herein, the ultrasonic instrument 20 may be a laparoscopic instrument that is held and manipulated by an operator. In another embodiment, the instrument may be a part of a surgical robotic arm. For example, the ultrasonic instrument may be coupled to a distal end of a robotic arm (e.g., arm 4 in FIG. 1), where movement and operation of the ultrasonic instrument may be performed via one or more user controls (e.g., UIDs, foot pedals, etc.) that are coupled to the surgical system. In some embodiments, the ultrasonic instrument may be coupled to an arm, and controlled by the generator based on user input. For example, the generator may control the rotational position of the hinged arm 31, so as to open or close the grasper 23 based on user input, via one or more user input devices, such as the UID 14, that are communicatively coupled to the generator, as described herein. In another aspect, the generator may adjust a spatial position (e.g., in space) of the end effector based on the user input (e.g., based on a position of the UID). In another aspect, the spatial position and/or the rotational position of the hinged arm may be controlled by the controller 40 (e.g., based on user input received by the controller).

As described herein, the surgical system is configured to estimate the temperature of the ultrasonic instrument, while the instrument is in a low-power state. In one aspect, the system may estimate this temperature based on user input. For example, the system may perform these estimation operations while the instrument is in this state, when the operator of the ultrasonic instrument is not actively using the instrument (e.g., to cut and/or seal tissue). Specifically, the operations are performed during a cooling cycle of the instrument. In another aspect, at least some of these operations may be performed while the instrument is being actively used to perform ultrasonic instrument operations. In particular, the controller 40 may perform closed-loop temperature controlling operations to maintain a particular end effector temperature while the operator is actively using the instrument. For example, the controller may estimate a temperature of the end effector, while the end effector is being actively used by the operator (e.g., while the instrument is in a high-power state, and while the blade of the end effector is producing heat due to friction between the blade and tissue that is being grasped by the end effector). In one aspect, the controller may estimate this "high-state" temperature using any known method (e.g., Adaptive Tissue Technology (ATT), Controlled Thermal Management (CTM), etc.), which estimate the temperature while the ultrasonic instrument is in a heating cycle. The controller may compare this high-state temperature with a temperature threshold. Upon determining that the high-state temperature is equal to or above (e.g., by a threshold amount) the temperature threshold, the controller may be configured to switch the ultrasonic instrument to the low-power state. Upon switching to the low-power state, the controller may continue to estimate the (e.g., "low-state") temperature of the blade, using one or more operations described herein. Upon determining that the low-state temperature is below the temperature threshold (or below this threshold by a threshold amount), the controller may be configured to reactive the ultrasonic instrument. Thus, the surgical system may regulate the current supplied to the ultrasonic instrument to maintain the temperature of the end effector.

As previously explained, an aspect of the disclosure may be a non-transitory machine-readable medium (such as microelectronic memory) having stored thereon instructions, which program one or more data processing components (generically referred to here as a "processor") to (automatically) perform ultrasonic instrument operations and/or temperature estimation operations, as described herein. In other aspects, some of these operations might be performed by specific hardware components that contain hardwired logic. Those operations might alternatively be performed by any combination of programmed data processing components and fixed hardwired circuit components.

While certain aspects have been described and shown in the accompanying drawings, it is to be understood that such aspects are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some aspects, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some aspects, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A method performed by a surgical system, the method comprising:
   providing current to an ultrasonic instrument to put the ultrasonic instrument in a low-power state, wherein the current is below a current threshold at which an end effector of the ultrasonic instrument produces heat; and
   while the ultrasonic instrument is in the low-power state:
      determining a resonance frequency of the end effector of the ultrasonic instrument;
      determining a temperature of the end effector based on the resonance frequency; and displaying, on a display of the surgical system, a notification based on the temperature.

2. The method of claim 1, wherein the end effector is a grasper that comprises 1) a blade that vibrates along a longitudinal axis of the blade and 2) a hinged jaw that is rotatably coupled to a joint of the grasper.

3. The method of claim 2, wherein the blade vibrates over a first excursion while the ultrasonic instrument is in a high-power state, and, while the ultrasonic instrument is in the low-power state the ultrasonic instrument draws less power to cause the blade to vibrate over a second excursion that is less than the first excursion.

4. The method of claim 2 further comprising determining that the grasper is in an open position in which the hinged jaw is rotated away from the blade, wherein the resonance frequency is determined in response to determining that the grasper is in the open position.

5. The method of claim 1 further comprising determining a baseline resonance frequency of the end effector during an initial powering up of the ultrasonic instrument, wherein the temperature of the end effector is determined based on a difference between the baseline resonance frequency and the resonance frequency.

6. The method of claim 5 further comprising determining a heating duration in which the ultrasonic instrument was in a high-power state prior to being in the low-power state, wherein determining the temperature of the end effector comprises using a predefined temperature model to output the temperature responsive to input based on the heating duration and the difference between the baseline resonance frequency and the resonance frequency.

7. The method of claim 1 further comprising providing, to the ultrasonic instrument, subsequent current greater than or equal to the current threshold to put the ultrasonic instrument in a high-power state in which end effector produces enough of the heat to cut or cauterize tissue.

8. The method of claim 1, wherein the resonance frequency is a first resonance frequency, wherein the method further comprises:
determining a second, subsequent, resonance frequency of the end effector while the ultrasonic instrument is in the low-power state; and
determining a time at which the temperature of the end effector will be below a threshold based on a rate of change between the first and second resonance frequencies,
wherein the notification includes the time.

9. The method of claim 1 further comprising:
determining whether the temperature is above a threshold; and
in response to determining that the temperature is above the threshold, at least one of 1) displaying the notification that includes text that indicates the temperature is high and 2) outputting output alert audio indicating that the temperature is high via one or more speakers of the surgical system.

10. A surgical system comprising:
an ultrasonic instrument with an end effector;
a display;
a processor; and
memory having instructions which when executed by the processor causes the surgical system to:
providing, to the ultrasonic instrument, current to put the ultrasonic instrument in a low-power state, wherein the current is below a current threshold at which the end effector produces heat; and
while the ultrasonic instrument is in the low-power state:
determine a resonance frequency of the end effector;
determine a temperature of the end effector based on the resonance frequency; and
display, on the display, a notification based on the temperature.

11. The surgical system of claim 10, wherein the end effector is a grasper that comprises 1) a blade that vibrates along a longitudinal axis of the blade and 2) a hinged jaw that is rotatably coupled to a joint of the grasper.

12. The surgical system of claim 11, wherein the blade vibrates over a first excursion while the ultrasonic instrument is in a high-power state, and, while the ultrasonic instrument is in the low-power state the ultrasonic instrument draws less power to cause the blade to vibrate over a second excursion that is less than the first excursion.

13. The surgical system of claim 11, wherein the memory has further instructions to determine that the grasper is in an open position in which the hinged jaw is rotated away from the blade, wherein the resonance frequency is determined in response to determining that the grasper is in the open position.

14. The surgical system of claim 10, wherein the memory has further instructions to determine a baseline resonance frequency of the end effector during an initial powering up of the ultrasonic instrument, wherein the temperature of the end effector is determined based on a difference between the baseline resonance frequency and the resonance frequency.

15. The surgical system of claim 14, wherein the memory has further instructions to determine a heating duration in which the ultrasonic instrument was in a high-power state prior to being in the low-power state, wherein the instructions to determine the temperature of the end effector comprises instructions to use a predefined temperature model to output the temperature responsive to input based on the heating duration and the difference between the baseline resonance frequency and the resonance frequency.

16. The surgical system of claim 10, wherein the notification includes the determined temperature of the end effector.

17. The surgical system of claim 10, wherein the resonance frequency is a first resonance frequency, wherein the memory has further instructions to:
determine a second, subsequent, resonance frequency of the end effector while the ultrasonic instrument is in the low-power state; and
determine a time at which the temperature of the end effector will be below a threshold based on a rate of change between the first and second resonance frequencies, wherein the notification includes the time.

18. The surgical system of claim 10, wherein the memory has further instructions to:
determine whether the temperature is above a threshold; and
in response to determining that the temperature is above the threshold, at least one of 1) display the notification that includes text that indicates the temperature is high and 2) output alert audio indicating that the temperature is high via one or more speakers of the surgical system.

19. A method performed by a surgical system, the method comprising:
providing current to an ultrasonic instrument that is below a current threshold at which the instrument causes a blade of the instrument to produce heat;

estimating, while the current is being provided to the ultrasonic instrument, a temperature of the blade based on a resonance frequency of the blade; and displaying, on a display, a notification based on the estimated temperature of the blade.

20. The method of claim 19, wherein the temperature of the blade is estimated without using a temperature sensor.

21. The method of claim 19, wherein the blade is arranged to vibrate along a longitudinal axis of the blade to produce the heat, wherein the blade is a part of a grasper of the ultrasonic instrument, the grasper also having a hinged arm that is arranged to rotate about an axis that is traverse to the longitudinal axis.

22. The method of claim 21 further comprising determining that the grasper is in an open position in which the hinged arm is rotated away from the blade, wherein the temperature is estimated in response to determining that the grasper is in the open position.

23. The method of claim 21 further comprising displaying, on the display, endoscopic video of a surgical site within a patient to which a surgical procedure is being performed, wherein the notification is a graphical user interface (GUI) item that is overlaid on top of the endoscopic video.

* * * * *